United States Patent [19]

Jung et al.

[11] Patent Number: 5,420,323
[45] Date of Patent: May 30, 1995

[54] ALLYLALKYLSILANES AND THEIR PREPARATION METHODS

[75] Inventors: Il N. Jung; Bok R. Yoo; Bong W. Lee; Mi-Yeon Suk, all of Seoul, Rep. of Korea

[73] Assignee: Korea Institute of Science and Technology, Seoul, Rep. of Korea

[21] Appl. No.: 302,429

[22] Filed: Sep. 8, 1994

[30] Foreign Application Priority Data

Dec. 1, 1993 [KR] Rep. of Korea ............... 26069/1993

[51] Int. Cl.$^6$ ........................... C07F 7/08; C07F 7/10; C07F 7/18
[52] U.S. Cl. .................................. 556/415; 556/482; 556/485; 556/489; 556/488; 556/465; 556/435; 549/215
[58] Field of Search ............... 556/482, 485, 489, 488, 556/465, 435, 415; 549/215

[56] References Cited

U.S. PATENT DOCUMENTS

| | | |
|---|---|---|
| 4,558,148 | 12/1985 | Ishikawa et al. .............. 556/488 |
| 4,864,027 | 9/1989 | Shubert et al. ................ 556/465 |
| 4,873,011 | 10/1989 | Jung et al. . |
| 4,876,363 | 10/1989 | Funahashi et al. ............ 549/215 |
| 4,965,385 | 10/1990 | Jung et al. . |
| 5,075,477 | 12/1991 | Jung et al. . |
| 5,233,069 | 8/1993 | Jung et al. . |
| 5,235,061 | 8/1993 | Jung et al. . |
| 5,235,083 | 8/1993 | Jung et al. . |
| 5,302,734 | 4/1994 | Jung et al. . |
| 5,332,849 | 7/1994 | Jung et al. . |
| 5,338,876 | 8/1994 | Jung et al. . |
| 5,342,984 | 8/1994 | Kubota et al. .............. 556/465 X |
| 5,359,106 | 10/1994 | Tabei et al. ................ 549/215 X |

*Primary Examiner*—Paul F. Shaver
*Attorney, Agent, or Firm*—Oblon, Spivak, McClelland, Maier & Neustadt

[57] ABSTRACT

The present invention relates to allylakylsilanes represented by the general formula (III) and their preparation methods by reacting allylsilanes represented by the formula I with olefin compounds represented by the formula II in the presence of hydrosilation catalysts such as chloroplatinic acid, platinum on silica, tributyl amine and Pd, Rh, Ni metals.

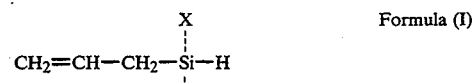

Formula (I)

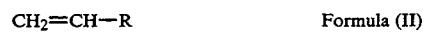

Formula (II)

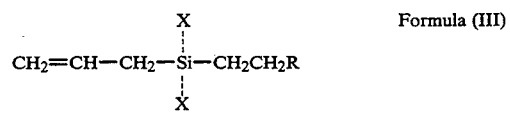

Formula (III)

wherein X represents independently chloro or alkoxy ($C_1$-$C_4$) and R is selected from the group consisting of Ph, $CH_2Cl$, $C_nH_{2n}CH_3$ (n=0-15), $Si(Me)_mCl_{3-m}$ (m=0-3), $CF_3$, $CH_2CF_3$, CN, $CH_2CN$,

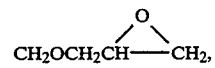

$CH_2Si(Me)_mCL_{3-m}$ (m=0-3), $Si(Me)_m(OR^1)_{3-m}$ (m=0-3), $CH_2Si(Me)_m(OR^1)_{3-m}$ (m=0-3), (wherein Me is methyl and $R^1$ is methoxy or ethoxy group), Ph-$CH_2Cl$, and cyclohexenyl group.

3 Claims, No Drawings

ALLYLALKYLSILANES AND THEIR PREPARATION METHODS

BACKGROUND OF THE INVENTION

1. Field of the Invention

The present invention relates to allylalkylsilanes represented by the general formula(III) and their preparation methods by reacting allylsilanes represented by the formula I with olefin compounds represented by the formula II in the presence of hydrosilation catalysts such as chloroplatanic acid, platinum on silica, tributyl amine and Pd, Rh, Ni metals.

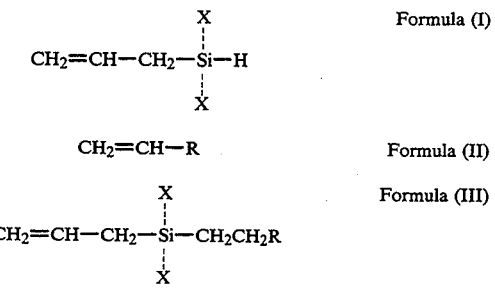

wherein X represents independently chloro or alkoxy $(C_1-C_4)$ and R is selected from the group consisting of Ph, $CH_2Cl$, $C_nH_{2n}CH_3$ (n=0-15), $Si(Me)_mCl_{3-m}$ (m=0-3), $CF_3$, $CH_{92}CF_3$, CN, $CH_2CN$,

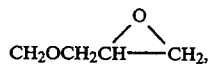

$CH_2Si(Me)_mCl_{3-m}$ (m=0-3), $Si(Me)_m(OR^1)_{3-m}$ (m=0-3), $CH_2Si(Me)_m(OR^1)_{3-m}$ (m=0-3) (wherein Me is methyl and $R^1$ is methoxy or ethoxy group), Ph-$CH_2Cl$, and cyclohexenyl group.

2. Description of the Prior Art

Direct synthesis of allyldichlorosilane was first reported by Hurd in 1945. (D. T. Hurd, J. Am. Chem. Soc., 67, 1813 (1945)) When allyl chloride was reacted with a 9:1 Si—Cu alloy, a vigorous exothemic reaction occurred even at 250° C. The condensate obtained contained trichlorosilane, tetrachlorosilane, allyldichlorosilane, diallyldichlorosilane, and allyltrichlorosilane predominating due to the decomposition of allyl chloride during the reaction. However, this reaction has never been used on a large scale in industry, because of the decomposition of allyl chloride and the easy polymerization of diallyldichlorosilane at high temperature above 130° C.

Mironov and Zelinskii reported later that they obtained only 644 g of a mixture of allylchlorosilanes from the reaction of a 5:1 Si—Cu alloy with 2 kg of allyl chloride at 300° C. The product mixture contained 356 g of allyldichlorosilane, 185 g of allyltrichlorosilane, and 103 g of diallyldichlorosilane. (V. M. Mironov and D. N. Zelinskii, Isvest. Akad. Nauk S.S.S.R., Otdel. Khim. Nauk 383 (1957)) The production of allyldichlorosilane and allyltrichlorosilane indicates that allyl chloride decomposed under the reaction conditions and dehydrochlorination or dechlorination were accompanied. This is why the yield was under 30%, indicating that the process was not economically feasible.

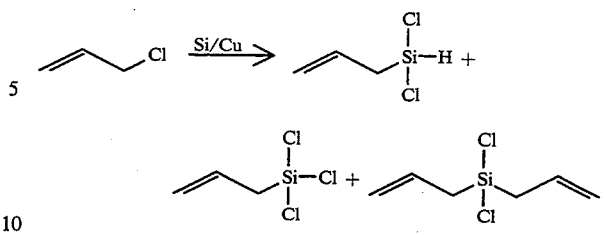

The present inventors reported a preparation method of allylchlorosilanes by directly reacting silicon metal simultaneously with allyl chloride and hydrogen chloride in the presence of copper catalyst at a temperature from 220° C. to 350° C. Allyldichlorosilane was obtained as the major product indicating one mole of each reactant reacted with the same silicon atom. When sufficient hydrogen chloride was added, diallyldichlorosilane was not formed. This eliminated the polymerization problem involved in the direct synthesis. (Korean Patent application No. 92-10292 (1992. 6. 13))

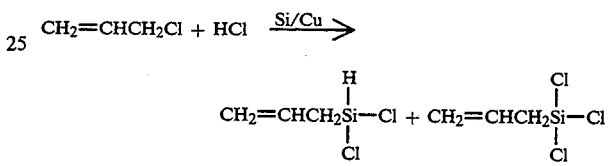

Since the chlorine groups on silicon are easily hydrolyzed and give highly toxic hydrogen chloride, chlorosilanes are reacted with alcohol and converted to the corresponding alkoxysilanes. Allyldichlorosilane is reacted with alcohol to give hydrogen chloride and allyldialkoxysilane. If inert organic solvents are used in the reaction, less hydrogen chloride is dissolved in the product and less hydrolyzed by-products due to the water produced from the reaction of hydrogen chloride and alcohol are produced. The hydrogen chloride dissolved in the product will cause the cleavage of Si—H bond. In this reaction organic amines such as pyridine or triethylamine can be used to capture the hydrogen chloride in the products. (W. Noll, "Chemistry and Technology of Silicones" Academic Press, New York, 1968)

Si—H containing organosilicon comounds can be hydrosilylated with carbon-carbon unsaturated compounds and various organic groups can be introduced through hydrosilation. This hydrosilation can occur, but proceeds better in the presence of noble metal catalysts such as platinum, chloroplatinic acid. The most common catalyst is chloroplatinic acid which is used as a solution in isopropanol. In addition to platinum and palladium, inorganic compounds of nickel, rhodium, ruthenium, copper, and tin may be used depending upon the nature of the unsaturated organic compounds. The organic catalysts other than metallic or inorganic compounds such as triethyl amine, triphenylphoshine, and dimethylformamide may also be used. (E. Y. Lukevites and M. G. Voronkov, "Organic Insertion Reactions of Group IV Elements", Consultants Bureau, New York 1966) The most generally used catalysts are platinum catalyst such as chloroplatinic acid, platium on silica, and platinum on carbon.

Addition reactions of hydrosilanes to unsaturated compounds is initiated thermally, by radicals, and by catalysts. At temperatures of about 300° C. without catalyst the hydrosilation occurs. Various organic peroxides which easily form free radicals have been used to initiate the hydrosilation. However, the thermal and radical reactions give many by-products and are not practical on a large scale. The hydrosilation proceeds better in the presence of noble metal catalysts such as platinum, palladium, etc.

SUMMARY OF THE INVENTION

The present invention relates to allylalkylsilanes represented by the general formul (III) and their preparation methods by reacting allylsilanes represented by the formula I with olefin compounds represented by the formula II the presence of hydrosilation catalysts such as chloroplatinic acid, platinum on silica, tributyl amine and Pd, Rh, Ni metals.

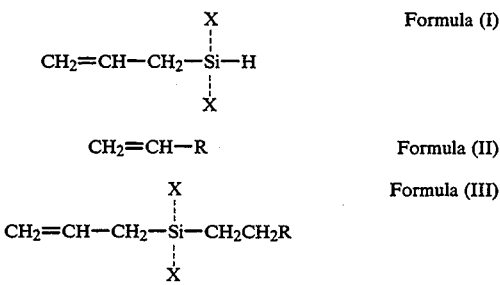

wherein X represents independently chloro or alkoxy ($C_1$–$C_4$) and R is selected from the group consisting of Ph, $CH_2Cl$, $C_nH_{2n}CH_3$ (n=0–15), $Si(Me)_mCl_{3-m}$(m=0–3), $CF_3$, $CH_2CF_3$, $CN$, $CH_2CN$,

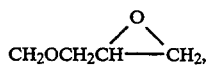

$CH_2Si(Me)_mCl_{3-m}$(m=0–3), $Si(Me)_m(OR^1)_{3-m}$(m=0–3), $CH_2Si(Me)_m(OR^1)_{3-m}$(m=0–3) (wherein Me is methyl and $R^1$ is methoxy or ethoxy group), Ph-$CH_2Cl$, and cyclohexenyl group.

DETAILED DESCRIPTION OF THE INVENTION

The hydrosilation reactions of allyldichlorosilane or allyldialkoxysilane of the present invention can be run in standard laboratory glasswares or commercial equipments, under inert atmosphere, with units for external heating and cooling, stirring, and for incremental addition of the start silanes or olefins. The reaction can be carried out in most of organic solvents, but it also proceeds in neat condition. When allyl chloride is hydrosilylated, the reactor should be pressurized because propylene gas is evolved as a by-product. Otherwise it is not necessary to pressurized the reactor because of the relative high boiling points of allyldichorosilane or allyldialkoxysilane.

In a typical preparation, olefin-compounds as represented by the formula II and the hydrosilation catalyst are placed in the reactor under inert atmosphere. Allyldichlorosilane is then slowly added to the solution with stirring. In any cases, the reverse addition must not be used, because allyldichlorosilane has two functional group necessary for hydrosilation, self polymerization occurs as soon as it contacts the catalyst. Therefore this hydrosilation reaction should be carried out using excess mount of olefin compound. The reactions may be sufficiently exothermic at controlled addition rates to maintain to reflux without continuous carrying out external heating. After completion of addition, heating may be carried out for a certain period of time to complete the hydrosilation and then the products may be fractionally distilled at atmosphere or under vacuum.

The invention will be further illustrated by the following examples. It is, however, not intended that this invention will be limited by the examples. In the following examples, temperatures are reported in degress Celsius. Abbreviations for nuclear magnetic resonance(NMR) spectra are s=singlet, d=doublet, t=triplet, m=multiplet; peak positions are reported as parts per million on the basis of the internal tetramethylsilane.

EXAMPLE 1

Synthesis of 4,4,7-trichloro-4-sila-1-heptene

To a 100 ml, three neck, round bottomed flask equipped with a mechanical stirrer, a dropping funnel, and a condenser were added under the dried nitrogen atmosphere, 542 g (7.08 mol) of allyl chloride and 600 µl of 1% chloroplatinie acid catalyst. Through the dropping funnel was added dropwise 100 g (0.71 mol) of allyldichlorosilane for 30 min while refluxing. After confirming by gas chromatography to complete the reaction, the product was fractionally distilled under vacuum (60°–64° C./0.5 torr) to give 95 g (62.5 %) of 4,4,7-trichloro-4-sila-1-heptene. Allyltrichlorosilane 30.0 g (19.7 %) was also obtained as a by-product.

EXAMPLE 2

Synthesis of 4,4-dichloro-7-phenyl-4-sila-hexene

Using the same apparatus and procedure described in EXAMPLE 1, 370 g (3.55 mol) of styrene and 500 µl of 1% chloroplatinic acid in isopropanol were added to the flask. Through the dropping funnel was added dropwise 50 g (0.35 mol) of allyldichlorosilane for 30 rain at 80° C. After confirming by gas chromatography to complete the reaction, vacuum distillation (96°–98° C.) of the product mixture gave 61 g (71%) of 4,4-dichloro-7-phenyl-4-sila-1-hexene.

EXAMPLE 3

Synthesis of 4,4-dichloro-4-sila-1-decene

Using the same apparatus and procedure described in EXAMPLE 1, 59.7 g (0.71 mol) of 1-hexene and 80 µl of 1% chloroplatinic acid in isopropanol were added to the flask. Through the dropping funnel was added dropwise 10 g (0.07 mmol) of allyldichlorosilane for 30 rain while refluxing. After confirming by gas chromatography to complete the reaction, vacuum distillation (48°–50° C./0.5 torr) gave 12.5 g (79.3%) of 4,4-dichloro-4-sila-1 -decene.

EXAMPLE 4

Synthesis of 4,4-dichloro-7-cyano4-sila-1-heptene

Using the same apparatus and procedure described in EXAMPLE 1, 97.9 g (1.46 mol) of allyl cyanide and 350 µl of 1% chloroplatinic acid in isopropanol were added to the flask. Through the dropping funnel was added dropwise 20.6 g (0.15 mmol) of allyldichlorosilane for 30 min at 80° C. and the solution was further reacted for 17.5 hrs to complete the reaction. Vacuum distillation (76–78/0.5 torr) of the product mixture gave 18.76 g (62%) of 4,4-dichloro-7-cyano-4-sila-1-heptene.

EXAMPLE 5

Synthesis of 7-methyl-4,4,7-trichloro-4,7-disila-1-octene

Using the same apparatus and procedure described in EXAMPLE 1, 25.3 g (0.21 mol) of vinyldimethylchlorosilane and 50 μl of 1% chloroplatinic acid in isopropanol were added to the flask. Through the dropping funnel was added dropwise 10 g (0.07 mol) of allyldichlorosilane for 30 rain at 80° C. and the solution was further reacted for 2 hrs to complete the reaction. Vacuum distillation (48°-52° C./0.5 torr) of the product mixture gave 16.2 g (89%) of 7-methyl-4,4,7-trichloro-4,7-disila-1-octene.

EXAMPLE 6

Synthesis of 6-(3-hexenyl)-4,4-dichloro-4-sila-1-hexene

Using the same apparatus and procedure described in EXAMPLE 1, 37.8 g (0.35 mol) of 4-vinylcyclohexene and 60 μl of 1% chloroplatinic acid in isopropanol were added to the flask. Through the dropping funnel was added dropwise 10.0 g (0.07 mmol) of allyldichlorosilane for 30 min at 80° C. and the solution was further reacted for 3 hrs to complete the reaction. Vacuum distillation (70-73° C./0.5 torr) of the product mixture gave 13.5 g (78%) of 6-(3-hexenyl)-4,4-dichloro-4-sila-1-hexene.

The compounds prepared by hydrosilating allyldichlorosilane with various unsaturated organic compounds according to the procedure described above are listed in Table 1.

EXAMPLE 7

Synthesis of 7-chloro-4,4-dimethoxy-4-sila-1-heptene

Using the same apparatus and procedure described in EXAMPLE 1, 7.7 g (0.1 mol) of allylchloride and 60 μl of 1% chloroplatinic acid catalyst were added to the flask. Through the dropping funnel was added dropwise 6.6 g (0.05 mmol) of allyldimethoxysilane for 30 min. while refluxing. After confirming by gas chromatography to complete the reaction, the product was fractionally distilled under vacuum (59°-62° C./0.5 torr) to give 8.0 g (81%) of 7-chloro-4,4-dimethoxy-4-sila-1-heptene.

EXAMPLE 8

Synthesis of 4,4-dimethoxy-7-glycidoxy-4-sila-1-heptene

Using the same apparatus and procedure described in EXAMPLE 1, 12.1 g (0.11 mmol) of allylglycidyl ether and 60 μl of 1% chloroplatinic acid in isopropanol were added to the flask. Through the dropping funnel was added dropwise 6.6 g (0.05 mmol) of allyldimethoxysilane at 80° C. and the solution was further reacted for 2 hrs to complete the reaction. Vacuum distillation (83°-85° C.) of the product mixture gave 5.3 g (43.5%) of 4,4-dimethoxy-7-glycidoxy-4-sila-1-heptene.

The compounds prepared by hydrosilating allyldimethoxysilane with various unsaturated organic compounds according to the procedure described above are listed in Table 2.

TABLE 1

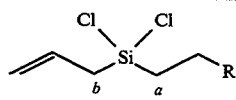

| R | SiCH$_2$(a) | CH$_2$ | SiCH$_2$(b) | =CH$_2$ | =CH | R |
|---|---|---|---|---|---|---|
| CH$_2$Cl | 1.25–1.31 | 1.94–2.04 | 2.11–2.15 | 5.08–5.15 | 5.71–5.82 | 3.35(t, 2H, CH$_2$) |
| CN* | 1.24–1.30 | 2.40 (t) | 2.10–2.13 | 5.08–5.14 | 5.70–5.81 | — |
| CH$_2$CN | 1.24–1.29 | 1.82–1.92 | 2.11–2.13 | 5.08–5.13 | 5.69–5.82 | 2.43(t, 2H, CH$_2$) |
| CF$_3$ | 1.25–1.32 | 2.02–2.39 | 2.12–2.16 | 5.09–5.14 | 5.70–5.82 | — |
| CH$_2$CF$_3$ | 1.22–1.33 | 1.83–1.93 | 2.11–2.14 | 5.08–5.15 | 5.70–5.83 | 2.03–2.39(m, 2H, CH$_2$) |
| CH$_3$ | 1.12–1.17 | 1.24–1.57 | 2.09–2.13 | 5.08–5.14 | 5.74–5.81 | 0.91(t, 3H, CH$_3$) |
| (CH$_2$)$_2$CH$_3$ | 1.11–1.16 | 1.23–1.56 | 2.09–2.16 | 5.07–5.12 | 5.75–5.85 | 0.91(t, 3H, CH$_3$), 1.23–1.56(m, 6H, CH$_2$) |
| (CH$_2$)$_{15}$CH$_3$ | 1.11–1.17 | 1.21–1.57 | 2.05–2.17 | 5.07–5.12 | 5.73–5.87 | 0.92(t, 3H, CH$_3$), 1.21–1.57(m, 28H, CH$_2$) |
| cyclohexenyl | 1.12–1.19 | 1.47–1.53 | 2.10–2.13 | 5.08–5.13 | 5.69–5.86 | 1.46–1.79(m, 3H, CH & CH$_2$), 2.07–2.13(m, 4H, CH$_2$), 5.67 (br, s, 2H, CH) |
| Ph | 1.47–1.53 | 2.83–2.88 | 2.03–2.06 | 5.04–5.11 | 5.68–5.82 | 7.21–7.33(m, 5H, Phenyl-H) |
| p-PhCH$_2$Cl | 1.48–1.52 | 2.81–2.88 | 2.03–2.05 | 5.04–5.12 | 5.67–5.81 | 4.54(s, 2H, CH$_2$Cl), 7.19–7.32 (m, 4H, Phenyl-H) |
| SiMe$_3$ | 0.89–0.96 | 0.75–0.82 | 2.13–2.14 | 5.08–5.15 | 5.69–5.77 | 0.01(s, 9H, CH$_3$) |
| SiMe$_2$Cl | 0.90–0.96 | 1.12–1.17 | 2.13–2.15 | 5.09–5.14 | 5.70–5.77 | 0.45(s, 6H, CH$_3$) |
| SiMeCl$_2$ | 0.90–1.19 | 0.90–1.19 | 2.14–2.16 | 5.09–5.15 | 5.70–5.78 | 0.83(s, 3H, CH$_3$) |
| SiCl$_3$ | 0.91–0.97 | 1.46–1.56 | 2.14–2.16 | 5.08–5.15 | 5.69–5.78 | — |
| CH$_2$SiMe$_3$ | 0.90–0.96 | 0.76–0.83 | 2.13–2.15 | 5.08–5.16 | 5.69–5.77 | 0.01(s, 9H, CH$_3$), 0.63–0.69(m, 2H, CH$_2$) |
| CH$_2$SiMe$_2$Cl | 0.90–0.96 | 1.12–1.18 | 2.12–2.14 | 5.08–5.14 | 5.71–5.77 | 0.44(s, 6H, CH$_3$), 1.11–1.19(m, 2H, CH$_2$) |
| CH$_2$SiMeCl$_2$ | 0.90–1.20 | 0.90–1.20 | 2.14–2.17 | 5.09–5.14 | 5.70–5.79 | 0.83(s, 3H, CH$_3$), 0.90–1.20 9m, 2H, CH$_2$) |
| CH$_2$SiCl$_3$ | 0.90–0.97 | 1.54–1.65 | 2.13–2.16 | 5.08–5.14 | 5.69–5.79 | 1.44–1.54 |

*Ni was used as the catalyst

TABLE 2

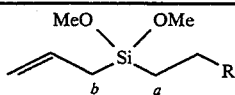

| R | SiCH₂(a) | CH₂ | SiCH₂(b) | =CH₂ | =CH | OCH₃(s) | R |
|---|---|---|---|---|---|---|---|
| CH₂Cl | 0.51–0.61 | 1.83–1.92 | 1.42–1.58 | 5.07–5.14 | 5.70–5.80 | 3.48 | 3.33(t, 2H, CH₂) |
| CN* | 0.49–0.60 | 2.38 (t) | 1.42–1.59 | 5.07–5.14 | 5.70–5.81 | 3.48 | — |
| CH₂CN | 0.49–0.60 | 1.79–1.87 | 1.41–1.59 | 5.07–5.13 | 5.69–5.81 | 3.48 | 2.41(t, 2H, CH₂) |
| CF₃ | 0.48–0.61 | 1.99–2.29 | 1.41–1.57 | 5.07–5.14 | 5.70–5.81 | 3.49 | — |
| CH₂CF₃ | 0.49–0.60 | 1.79–1.89 | 1.42–1.59 | 5.07–5.15 | 5.70–5.80 | 3.48 | 2.02–2.38(m, 2H, CH₂) |
| (CH₂)₂CH₃ | 0.46–0.59 | 1.16–1.66 | 1.35–1.55 | 5.08–5.13 | 5.71–5.83 | 3.47 | 0.90(t, 3H, CH₃), 1.16–1.66(m, 4H, (CH₂)₄ |
| (CH₂)₁₅CH₃ | 0.46–0.60 | 1.15–1.67 | 1.35–1.55 | 5.07–5.14 | 5.72–5.83 | 3.47 | 0.92(t, 3H, CH₃), 1.15–1.67(m, 28H, CH₂) |
| 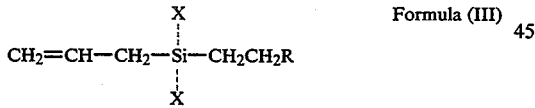 | 0.45–0.60 | 1.47–1.53 | 1.39–1.56 | 5.08–5.13 | 5.68–5.84 | 3.48 | 1.46–1.78(m, 3H, CH & CH₂), 2.05–2.10(m, 4H, CH₂), 5.62(br.s, 2H, CH) |
| Ph | 0.50–0.61 | 2.80–2.86 | 1.43–1.60 | 5.03–5.12 | 5.68–5.82 | 3.47 | 7.18–7.31(m, 5H, Phenyl-H) |
| p-PhCH₂Cl | 0.49–0.61 | 2.79–2.85 | 1.52–1.61 | 5.04–5.11 | 5.67–5.83 | 3.47 | 4.53(s, 2H, CH₂Cl), 7.19–7.32(m, 4H, Phenyl-H) |
| 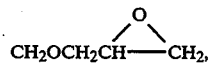 | 0.59–0.64 | 1.55–1.66 | 1.60–1.63 | 4.83–4.94 | 5.70–5.79 | 3.48 | 2.52–2.74(m, 2H, CH₂), 3.05–3.10(m, 1H, CH), 3.28–3.67(m, 4H, CH₂) |
| SiMe₃ | 0.45–0.58 | 0.45–0.58 | 1.52–1.60 | 5.05–5.14 | 5.68–5.76 | 3.48 | 0.01(s, 9H, CH₃) |
| SiMe₂OMe | 0.46–0.63 | 0.46–0.63 | 1.48–1.61 | 5.07–5.12 | 5.71–5.78 | 3.48 | 0.10(s, 6H, CH₃), 3.54(s, 3H, OCH₃) |
| Si(OMe)₃ | 0.45–0.62 | 0.45–0.62 | 1.49–1.60 | 5.08–5.13 | 5.70–5.79 | 3.47 | 0.20(s, 3H, CH₃), 3.53(s, 6H, OCH₃) |
| CH₂SiMe₃ | 0.45–0.61 | 0.45–0.61 | 1.48–1.60 | 5.07–5.14 | 5.70–5.77 | 3.48 | 3.53(s, 9H, OCH₃) |
| CH₂SiMe₂OMe | 0.45–0.62 | 0.45–0.62 | 1.49–1.61 | 5.08–5.14 | 5.69–5.78 | 3.48 | 0.01(s, 9H, CH₃), 3.54(s, 3H, OCH₃) |
| CH₂SiMe₂(OMe)₂ | 0.45–0.61 | 0.45–0.61 | 1.49–1.60 | 5.07–5.13 | 5.70–5.78 | 3.47 | 0.02(s, 9H, CH₃), 3.54(s, 6H, OCH₃) |
| CH₂Si(OMe)₃ | 0.44–0.60 | 0.44–0.60 | 1.48–1.60 | 5.06–5.14 | 5.69–5.78 | 3.47 | 3.53(s, 9H, OCH₃) |

*Ni was used as the catalyst.

Hydrosilation of allyldiethoxysilane with various olefins in the presence of chloroplatinic acid catalyst according to the procedures described above gave the corresponding allylorganodiethoxysilanes as listed in Table 2. NMR data of the compounds were similar to those of the corresponding allylorganodimethoxysilanes except the peaks due to the alkoxy groups.

What is claimed is:

1. Allylalkylsilanes represented by the formula (III)

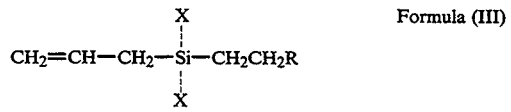   Formula (III)

wherein X represents independently chloro or alkoxy (C₁–C₄) and R is selected from the group consisting of Ph, CH₂Cl, C$_n$H$_{2n}$CH₃ (n=0–15), Si(Me)$_m$Cl$_{3-m}$(m=0–3), CF₃, CH₂CF₃, CN, CH₂CN,

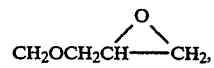

CH₂Si(Me)$_m$Cl$_{3-m}$(m=0–3), Si(Me)$_m$(OR¹)$_{3-m}$(m=0–3), CH₂Si(Me)$_m$(OR¹)$_{3-m}$(m=0–3) (wherein Me is methyl and R¹ is methoxy or ethoxy group), Ph-CH₂Cl, and cyclohexenyl group.

2. A method for preparation of the compounds of the formula (III) according to claim 1 which comprises hydrosilating allylsilanes represented by the formula (I)

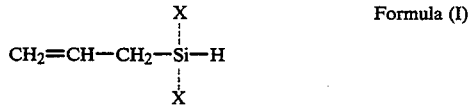   Formula (I)

with olefin compounds represented by the formula (II) in the presence of hydrosilating catalyst.

   Formula (II)

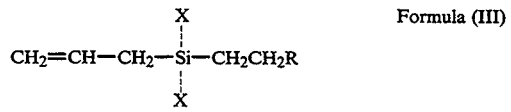   Formula (III)

wherein X represents independently chloro or alkoxy (C₁–C₄) and R is selected from the group consisting of Ph, CH₂Cl, C$_n$H$_{2n}$CH₃ (n=0–15), Si(Me)$_m$Cl$_{3-m}$(m=0–3), CF₃, CH₂CF₃, CN, CH₂CN,

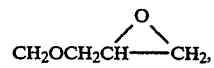

CH₂Si(Me)$_m$Cl$_{3-m}$(m=0–3), Si(Me)$_m$(OR¹)$_{3-m}$(m=0–3), CH₂Si(Me)$_m$(OR¹)$_{3-m}$(m=0–3) (wherein Me is methyl and R¹ is methoxy or ethoxy group), Ph-CH₂Cl, and cyclohexenyl group.

3. The method according to claim 2, wherein the hydrosilation catalyst comprises at least one comound selected from the group consisting of chloroplatinic acid, platinum on silica, tributyl amine and inorganic compounds of Pd, Rh, or Ni.

* * * * *